United States Patent
Kanodia et al.

(10) Patent No.: US 10,245,067 B2
(45) Date of Patent: Apr. 2, 2019

(54) REUSABLE LOCKING SAFETY SCALPEL

(71) Applicant: Ribbel International Limited, Delhi (IN)

(72) Inventors: Rajendra Kanodia, Delhi (IN); Vikram Kanodia, Delhi (IN); Avinash Kanodia, Delhi (IN)

(73) Assignee: Ribbel International Limited, New Delhi (IN)

( * ) Notice: Subject to any disclaimer, the term of this patent is extended or adjusted under 35 U.S.C. 154(b) by 22 days.

(21) Appl. No.: 15/270,590

(22) Filed: Sep. 20, 2016

(65) Prior Publication Data
US 2017/0189048 A1  Jul. 6, 2017

(30) Foreign Application Priority Data
Dec. 31, 2015  (IN) .......................... 4351/DEL/2015

(51) Int. Cl.
*A61B 17/3211* (2006.01)
*A61B 90/00* (2016.01)

(52) U.S. Cl.
CPC .......... *A61B 17/3211* (2013.01); *A61B 90/08* (2016.02); *A61B 2017/32113* (2013.01); *A61B 2090/0801* (2016.02)

(58) Field of Classification Search
CPC ................ A61B 17/3211; A61B 90/08; A61B 2017/32113; A61B 2090/0801
USPC ..................................... 30/162–163; 606/167
See application file for complete search history.

(56) References Cited

U.S. PATENT DOCUMENTS

| | | | |
|---|---|---|---|
| 5,330,493 A * | 7/1994 | Haining | A61B 17/3211 30/151 |
| 5,431,672 A * | 7/1995 | Cote | A61B 17/3211 30/167 |
| 5,531,754 A * | 7/1996 | Shackelford, Sr. | A61B 17/3211 30/162 |
| 6,022,364 A * | 2/2000 | Flumene | A61B 17/3211 606/166 |
| 6,589,258 B2 * | 7/2003 | Pilo | A61B 17/3213 606/167 |
| 6,757,977 B2 | 7/2004 | Dambal et al. | |
| 7,101,382 B2 * | 9/2006 | George | A61B 17/3211 30/162 |
| 7,900,362 B2 * | 3/2011 | Djordjevic | A61B 17/3213 30/162 |
| 8,819,943 B2 | 9/2014 | Maxwell | |

* cited by examiner

*Primary Examiner* — Ghassem Alie
*Assistant Examiner* — Nhat Chieu Do
(74) *Attorney, Agent, or Firm* — Alix, Yale & Ristas, LLP

(57) ABSTRACT

A reusable locking surgical scalpel with a housing, reciprocator assembly carrying a blade and an end cap. The reciprocator assembly includes a slider positioned outside the housing and wings that flex inward against the housing inner track. The reciprocator assembly and housing include locking members that cooperate with one another to maintain the blade in a cutting position forward of the housing front end. The wings may engage openings in the housing to releasably maintain the reciprocator assembly in an intermediate position rearward of the cutting position with the blade concealed within the housing. The end cap includes a locking member that engages the reciprocator assembly in a permanent locked position rearward of the intermediate position.

14 Claims, 5 Drawing Sheets

“A Novel Reusable Safety-Lock Equipped Scalpel and Mode of Working for Same”, the entire disclosure of which is hereby incorporated by reference.

REUSABLE LOCKING SAFETY SCALPEL

RELATED APPLICATION

This application claims priority from Indian Patent Application No. 4351/DEL/2015 filed Dec. 31, 2015, for "A Novel Reusable Safety-Lock Equipped Scalpel and Mode of Working for Same", the entire disclosure of which is hereby incorporated by reference.

BACKGROUND

The disclosure relates to surgical scalpels, and more particularly to a reusable scalpel with a locking mechanism.

In order to minimize any danger of accidental injury all currently produced surgical scalpels feature means to cover or otherwise conceal the sharp edge of the blade whenever the scalpel is not deployed for use, including prior to disposal after the use. Typical commercial products include scalpels with separate blade covers or a retractable scalpel assembly that allows optional concealment of the blade. Retractable products are commonly preferred in the medical industry due to their more streamlined designs with fewer separate parts, and more facile operation ideally with only a single hand. Existing retractable products carry numerous drawbacks, including having unsteady blades and either (a) not permanently concealing or protecting the blade or (b) permanently concealing the blade, but not being reusable. It would thus be useful to have a reusable scalpel that is operable with one hand and allows permanent protection of the blade without any separate parts.

SUMMARY

A surgical scalpel has a housing, reciprocator assembly, blade and end cap. The housing defines a housing axis and has a front, a back and opposite sides. One side defines an axial track that extends from the housing back to a closed front end rear of the housing front. The reciprocator assembly has a slider connected to an elongate blade carrier. The blade carrier is positioned within the housing and extends from a front to a rear along the housing axis. The slider is positioned outside the housing and is connected to the blade carrier through the track. The blade carrier includes a first lock member proximate its rear. The end cap is attachable to the housing proximate the housing back and defines a second lock member for cooperation with the first lock member. The housing also defines a third lock member forward of the track front end and the slider defines a fourth lock member for cooperation with the third lock member. The reciprocator assembly is axially reciprocable from an initial position with the blade concealed within the housing to a cutting position with the blade exposed from the front of the housing and the third and fourth lock member in releasable engagement with each other to maintain the reciprocator and housing axially relative to one another. Optional disengagement of the third lock member from the fourth lock member allows rearward reciprocation of the reciprocator assembly to a disposing position with the reciprocator assembly rear of the initial position and the first lock member engaged with the second lock member in a permanent attachment.

In another embodiment, a surgical scalpel has an elongate housing, reciprocator assembly, blade and end cap. The housing extends longitudinally from a back to a front and includes opposite sides spaced from one another via upper and lower edges. The housing defines a longitudinal track in at least one side. The reciprocator assembly has a flat elongate portion positioned within the housing which is attachable to the blade. The reciprocator assembly has a first locking member and a pair of opposing wings extending obliquely from opposite edges of the flat elongate portion in the direction of the upper and lower edges. The blade has a cutting edge and is secured to the blade carrier and projects forward of the carrier. The end cap is attachable to the housing proximate the back and defines a second lock member for cooperation with the first lock member. The upper and lower edges of the housing each includes an indentation at a position intermediate the front and back for receipt of a wing in a releasable engagement to maintain the reciprocator assembly in an initial position with the blade concealed within the housing. The reciprocator assembly is longitudinally reciprocable from the initial position to a cutting position with the cutting edge of the blade exposed from the front end of the housing and longitudinally reciprocable to a disposing position with the reciprocator assembly rear of the initial position and longitudinally locked to the end cap.

BRIEF DESCRIPTION OF THE DRAWINGS

Embodiments of the invention will be described in greater detail below with reference to the accompanying drawing, in which.

DETAILED DESCRIPTION

Figure 1:
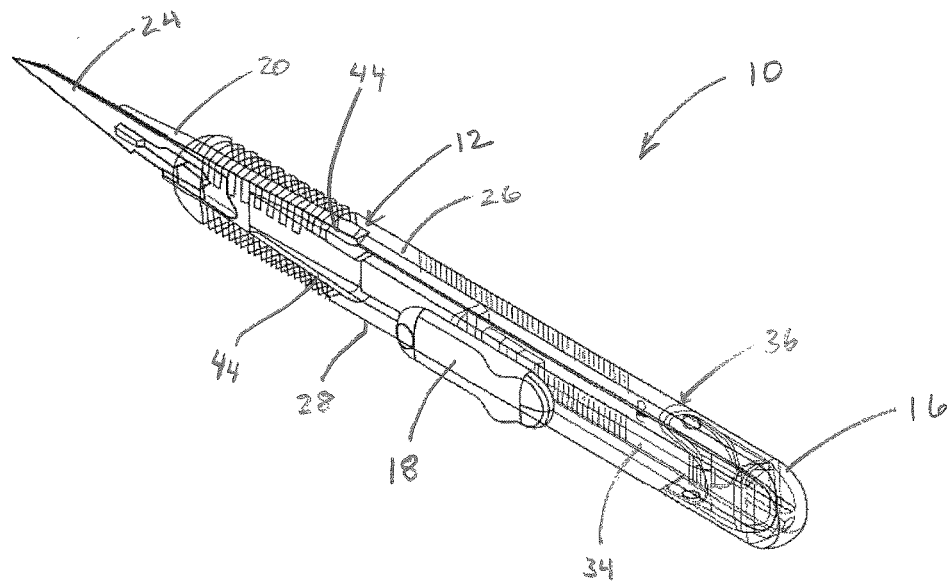
FIG. 1 is a perspective skeletal view of an embodiment of the disclosed scalpel in the cutting position.
Figure 2:
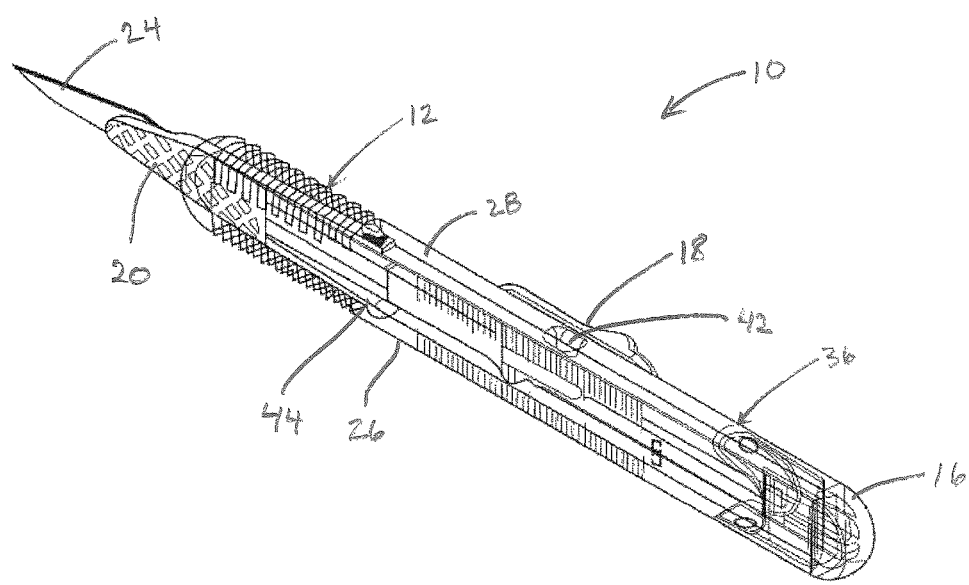
FIG. 2 is a perspective skeletal view of the scalpel showing the opposite side from FIG. 1.

With reference first to FIGS. 1-4, the disclosed surgical scalpel 10 includes three main components: a housing 12 with a reciprocator assembly 14 and end cap 16. As shown, the housing 12 is a longitudinally extending body defining an inner track 22 (see FIG. 6) for maintaining an elongate blade carrier portion 20 of the reciprocator assembly 14. As shown, the blade carrier 20 attaches to a blade 24 with the blade extending forward of the carrier. The housing 12 has a top edge 26 and bottom edge 28 extending between opposing sides 30 and 32. At least one side 32 defines a longitudinal slot 34 extending from proximate the rear 36 of the housing to a closed stop 38 intermediate the housing rear 36 and front 37. The side slot 34 defines an opening through which an intermediate coupler 40 connecting the blade carrier 20 with a slider 18 extends. During operation of the scalpel 10, the slot 34 acts as a guide allowing the reciprocator assembly 14 (carrying the blade 24) to be reciprocated forward and rearward via forward and rearward manipulation of the slider 18.

Figure 7:
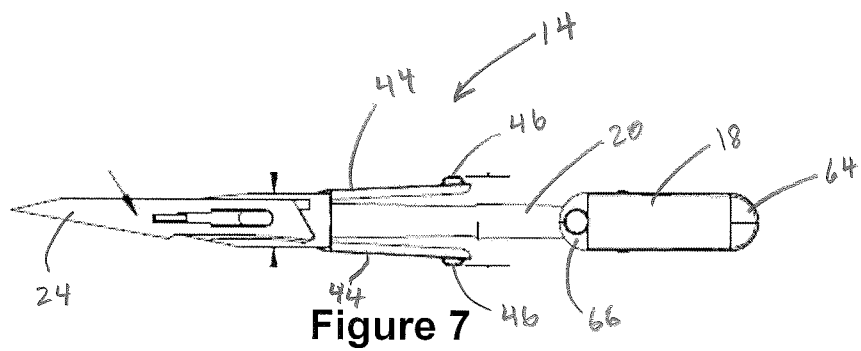
FIG. 7 is a side elevation view of the reciprocator assembly of the disclosed scalpel.

The housing 12 may also include at least one opening 42 in at least one of the upper and lower edges 26 and 28. As shown most clearly in FIGS. 7 and 8, the reciprocator assembly includes two wings 44 extending obliquely from the blade carrier in the direction of the upper and lower edges 26 and 28 of the housing. The wings 44 are configured to flex inward against the top and bottom edges (26 and 28) when the blade carrier portion 20 of the reciprocator assembly is inserted in to the housing track 22. In the preferred embodiment shown in the Figures, both of the upper and lower housing edges includes an opening 42. Each opening 42 in the respective edge of the housing is sized and shaped to cooperate with a proximal portion of a wing 44 to releasably maintain the reciprocator assembly 14 in an intermediate position between a cutting position and rear locked position (described in detail below). As depicted, each wing 44 includes a nub 46 for aiding engagement with the openings 42.

Figures 5A, 5B:
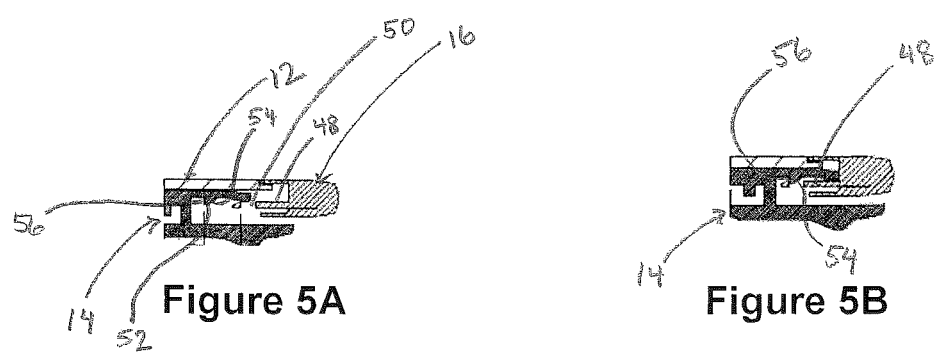
FIG. 5A is an enlarged section view of the end cap of the scalpel showing with the reciprocator assembly in an intermediate position.
FIG. 5B is an enlarged section view of the end cap of the scalpel maintaining the reciprocator assembly in a permanently locked position.

As shown in the partial section views of FIGS. 5A and 5B, the end cap 16 includes a flange 48 extending longitudinally forward and defining a second lock member with a slot 50. The reciprocator assembly 14 includes a first lock member with a rear tooth 52 with a rear ramped surface 54 transitioning to a front shoulder 56. The tooth 52 is positioned in alignment with the flange 48 to be received and maintained by the slot 50. As the reciprocator assembly 14 is slid rearward, the ramp 54 guides the tooth over the flange 48 until the tooth is received by the slot 50 to lock the reciprocator assembly 14 to the end cap 16. Either or both of the reciprocator assembly 14 and flange 48 may flex slightly to accommodate the other element during this sliding process. In the depicted embodiments, the rear of the housing element 12 is initially opened and configured for mating with a separate end cap 22 that closes the rear. Here, the end cap 22 and housing 12 include cooperating elements of a snapped attachment mechanism, such as teeth that engage notches. Alternate embodiments exist with the end cap and housing molded as a singular unit.

Figure 3:
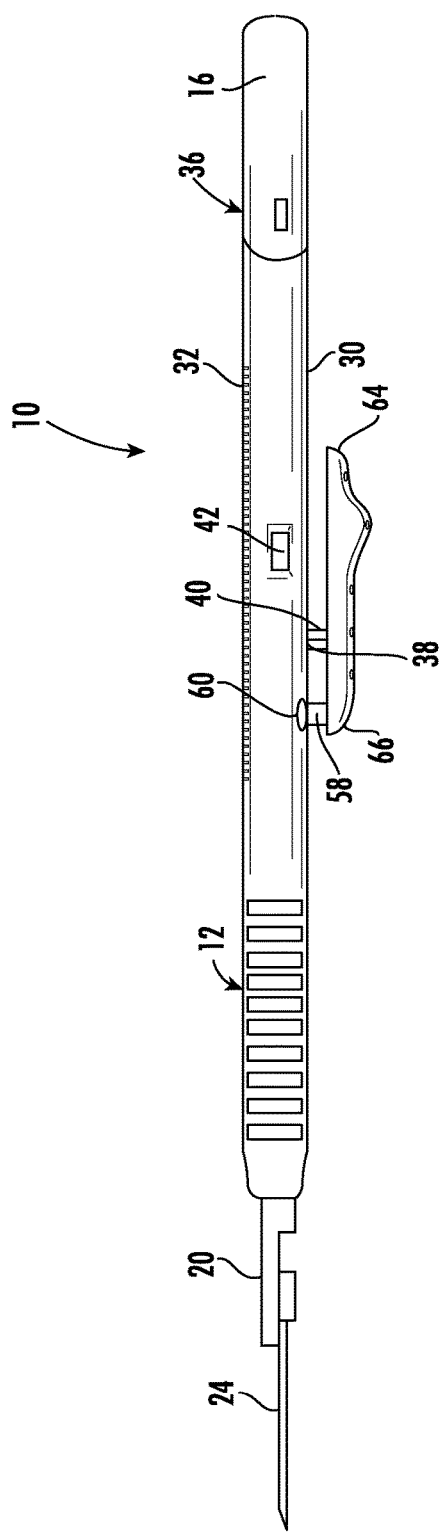
FIG. 3 is an elevation skeletal view of the scalpel in the cutting position from the top.
Figure 4:
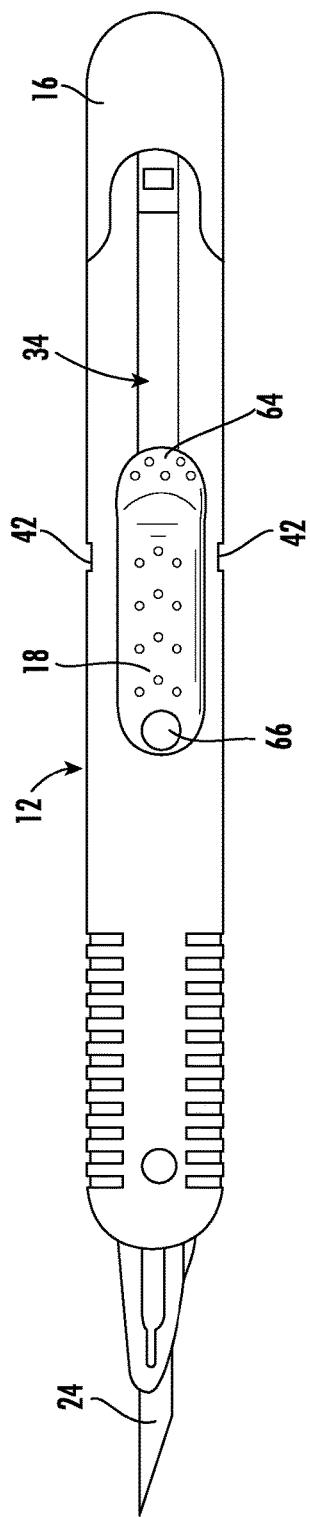
FIG. 4 is an elevation skeletal view of the scalpel in the cutting position from the side.
Figure 8:
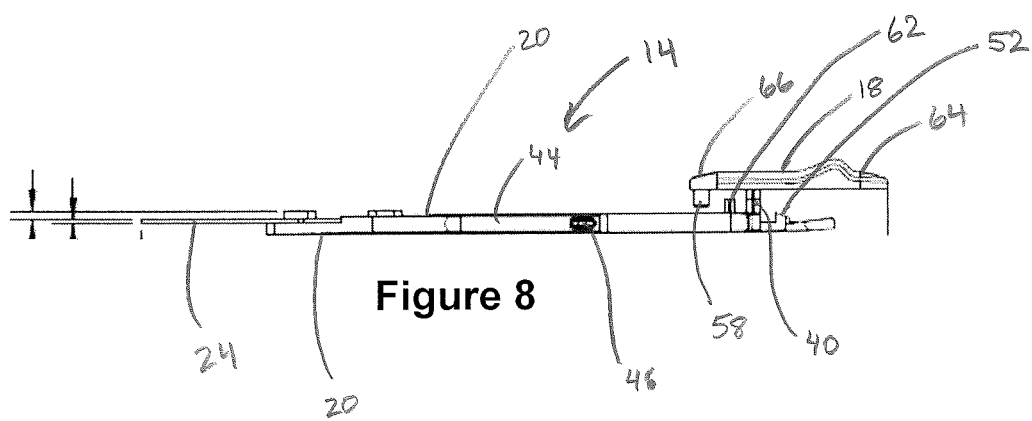
FIG. 8 is a top elevation view of the reciprocator assembly.

With reference to FIGS. 3 and 8, the slider 18 also includes a fourth lock member comprising a first projection 58 extending in the direction toward the housing. The housing 12 includes a third lock member comprising a recess or hole 60 forward of the slot forward stop 38. The recess 60 is sized and shaped to receive the first projection 58. The reciprocator assembly 14 includes a second projection 62 positioned longitudinally intermediate the coupler 40 and the first projection 58, and extending from the blade carrier 20 in the direction toward the first projection 58. The stop 38 at the front of the side slot 34 preferably has a ramped surface for guiding the first projection past the stop, but which abuts the second projection, thereby "stopping" forward reciprocation of the reciprocator assembly 14. The first projection 58, second projection 62, stop 38 and recess 60 are positioned relative to one another such that the first projection 58 is received by the recess 60 forward of the stop 38 as the second projection 62 abuts the stop 38. Engagement between the first projection 58 and the recess 60 prevents rearward manipulation of the reciprocator assembly 14, while abutment of the second projection 62 against the stop 38 prevents forward manipulation. The coupler 40 connecting the blade carrier 20 to the slider 18 through the slot 34 allows relative flexibility between the slider and blade carrier. As such, the first projection 58 can be released from engagement with the recess 60 by pressing or pinching a rear portion 64 of the slider 18 toward the housing 12, causing the front portion 66 of the slider to flex away from the housing 12.

Figure 6:
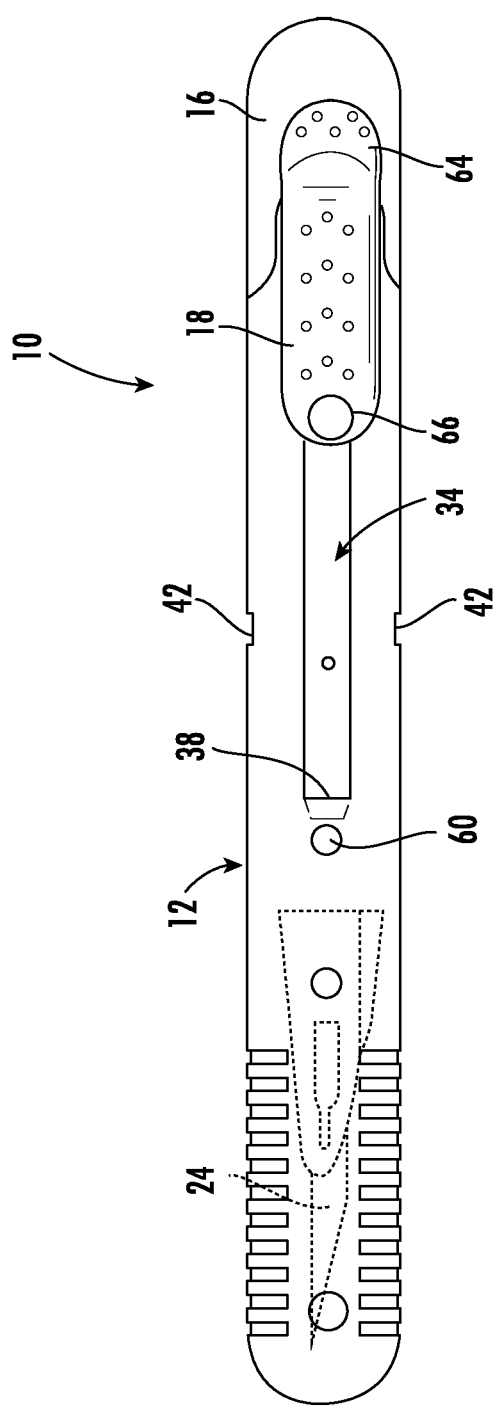
FIG. 6 is a skeletal view of the scalpel in the locked position.

Typically, the scalpel 10 arrives in a sealed package with the blade 24 concealed within the housing 12 and the reciprocator assembly 14 in a position intermediate the forward cutting position (FIGS. 1-4) and the rearward locked position (FIGS. 5B and 6). This initial intermediate position can be with the reciprocator assembly 14 at a longitudinal position with the distal portion of the wings 44 slightly rearward of the openings 42 in the upper and lower housing edges, 26 and 28. Alternatively, the initial intermediate position can be with the reciprocator assembly 14 at a longitudinal position with the wings 44 maintained in the openings 42. A user may move the slider 20 longitudinally forward, thereby reciprocating the blade carrier 20 and exposing the blade 24 from the front end of the housing until the second projection 62 on the reciprocator assembly abuts the stop 38 with the first projection 58 aligned with the recess 60 in the housing. As noted above, the cooperation of the first projection 58 with the recess 60, and the second projection 62 with the stop 38 creates a condition wherein the reciprocator assembly 14 maintains the scalpel 10 in a cutting position with the blade 24 exposed forward of the housing 12 rigidly held relative to the housing.

As desired, a user can disengage the first projection 58 from the recess 60 via pressing the rear portion 64 of the slider 18 inward toward the housing 12, and then reciprocate the slider 18 rearward to conceal the blade 24 within the housing. At various points during a typical surgical procedure, a user may wish to conceal the blade 24 for safety without permanently locking it such that the scalpel can be used again during the procedure. The scalpel 10 makes such reuse possible by the releasable engagement of the wings 44 which cooperate with openings 42 in the upper and lower edges of the housing 12. For example, a user may reciprocate the slider 18 rearward until the nubs 46 at the distal portion each of the respective wings 44 engages with an opening 42, which will maintain the reciprocator assembly 14 in such an intermediate position with the blade 24 concealed. The reciprocator assembly 14 will be maintained in this position until the wing/opening engagement is broken by forcing the slider forward for reuse of the scalpel or rearward for locking.

Once the surgical procedure is complete (or at another point when locking the blade within the housing is desired), the slider 18 can be reciprocated rearward to a locked position depicted generally in FIGS. 5B and 6. As shown in the enlarged view of FIGS. 5A and 5B, the end cap 16 includes a flange 48 that defines a slot 50 configured to receive the tooth 52 in the reciprocator assembly 14. The tooth 52 is preferably shaped with a ramped rear edge 54 to aid in sliding over the front edge of the flange 48, and a substantially flat front edge 56. The flat configuration of the front edge 56 prevents the reciprocator assembly 14 from being reciprocated forward after the slot 50 engages the tooth 52, and consequently, the blade 24 is permanently locked concealed within the housing 12 (i.e., the locked position; FIGS. 5B and 6). The scalpel 10 can thereafter be disposed of safely without risk of accidental exposure of the blade. The only way to disengage the tooth 52 and slot 50 is by breaking the attachment of the end cap 16 and housing 12.

As described herein, the disclosed scalpel 10 offers a convenient reusable device that may maintain the blade in numerous longitudinal positions—exposed for use, intermediately maintained concealed for reuse or locked for disposal. In a preferred embodiment, the housing 12, reciprocator assembly 14 and end cap 16 are all formed from a plastic material. However, this is a nonlimiting characteristic of the scalpel.

While a preferred embodiment has been set forth for purposes of illustration, the foregoing description should not be deemed a limitation of the invention herein. Accordingly, various modifications, adaptations and alternatives may occur to one skilled in the art without departing from the spirit of the invention and scope of the claimed coverage.

What is claimed is:

1. A surgical scalpel comprising:
  a housing defining a housing axis and having a front, a back and opposite first and second sides enclosing an axial track, the first side defining an axial slot extending from the housing back to a closed front end positioned rear of the housing front;
  a reciprocator assembly with a slider connected to an elongate blade carrier, the blade carrier positioned within the housing extending from a front to a rear along the housing axis and the slider positioned outside the housing connected to the blade carrier through the slot, the slider having a front portion and a rear butt portion and the blade carrier including a first lock member proximate the rear of the reciprocator assembly;
  a blade secured to the blade carrier and projecting forward of the carrier, the blade having a cutting edge; and
  an end cap attachable to the housing proximate the housing back, the end cap defining a second lock member for cooperation with the first lock member, wherein
  the housing further defines a third lock member comprising a recess in the first side of the housing positioned forward of the closed front end of the slot and the slider defines a fourth lock member comprising a projection extending from the front portion of the slider toward the first side of the housing for cooperation with the third lock member, whereby the reciprocator assembly is axially reciprocable from an initial position with the blade concealed within the housing to a cutting position with the blade exposed from the front of the housing and the projection of the fourth lock member received by the recess of the third lock member in a releasable engagement to maintain the reciprocator and housing axially relative to one another, applying a force on the rear butt of the slider toward the first side of the housing to cause the slider to pivot and the projection to move away from the first side of the housing and disengage from the recess of the third lock member thereby allows rearward reciprocation of the reciprocator assembly to a locked position with the reciprocator assembly rear of the initial position and the first lock member engaged with the second lock member in a permanent attachment.

2. The surgical scalpel of claim 1, wherein one of the third and fourth lock members is a recess and the other of the third and fourth lock members is a projection sized and shaped to engage with the recess.

3. The surgical scalpel of claim 2, wherein the third lock member is an indentation in the housing and the fourth lock member is projection from the slider.

4. The surgical scalpel of claim 1, wherein the reciprocator assembly includes a pair of wings extending obliquely from the elongate blade carrier.

5. The surgical scalpel of claim 4, wherein the housing includes at least one recess on an inner surface for receiving a portion of at least one of the pair of wings to releasably maintain the reciprocator assembly in the initial position.

6. The surgical scalpel of claim 5, wherein the housing recess is an opening in at least an upper or lower edge of the housing.

7. The surgical scalpel of claim 1, wherein the end cap is removable from the housing.

8. The surgical scalpel of claim 1, wherein one of the first and second lock members is a tooth and the other of the first and second lock members is a slot sized and posited to receive the tooth.

9. The surgical scalpel of claim 1, wherein the first lock member is a tooth projecting from the blade carrier and the second lock member defines a slot for axially maintaining the tooth.

10. The surgical scalpel of claim 1, wherein the reciprocator assembly includes a second projection that abuts the closed front end of the housing track to prevent forward reciprocation of the blade in the cutting position.

11. The surgical scalpel of claim 1, wherein the recess of the third lock member is a hole defined in the first side of the housing.

12. A surgical scalpel comprising:
  an elongate housing extending longitudinally from a back to a front and including opposite first and second sides spaced from one another via upper and lower edges, the housing defining a longitudinal slot in the first side, the slot having a closed front end positioned rear of the housing front;
  a reciprocator assembly with a flat elongate portion extending from a front end to a rear end and positioned within the housing and being attachable to a blade, the reciprocator assembly having a pair of opposing wings extending obliquely from opposite edges of the flat elongate portion in the direction of the upper and lower edges, and a first lock member at the rear end of the reciprocator assembly, the first lock member comprising a tooth;
  a blade secured to the reciprocator assembly at the front end and projecting forward of the front end, the blade having a cutting edge;
  an end cap attachable to the housing proximate the housing back, the end cap defining a second lock member comprising a slot for receipt of the tooth of the first lock member, wherein
  the upper and lower edges of the housing each includes an indentation at a position intermediate the front and back for receipt of at least one of the pair of opposing wings in a releasable engagement to maintain the reciprocator assembly in an initial position with the blade concealed within the housing, and the reciprocator assembly is longitudinally reciprocable from the initial position to a cutting position with the cutting edge exposed from the front of the housing and longitudinally reciprocable to a locked position with the reciprocator assembly rear of the initial position and longitudinally locked to the end cap with the tooth of the first lock member maintained by the slot of the second lock member, and
  the housing further defines a third lock member comprising a recess in the first side of the housing positioned forward of the closed front end of the slot and the reciprocator assembly comprises a slider positioned outside the housing, the slider having a front end and a rear butt, the slider further defining a fourth lock member comprising a projection extending from the front end toward the first side of the housing for cooperation with the third lock member, whereby in the cutting position, the projection of the fourth lock member is received by the recess of the third lock member in a releasable engagement to maintain the reciprocator assembly and housing axially relative to one another, and applying a force on the rear butt of the slider toward the first side of the housing causes the slider to pivot and the projection to move away from the first side of the housing to disengage from the recess of the third lock member.

13. The surgical scalpel of claim 12, wherein the endcap is removable from the housing.

14. The surgical scalpel of claim 12, wherein the recess of the third lock member is a hole defined in the first side of the housing.

* * * * *